United States Patent [19]

Kilham et al.

[11] Patent Number: 4,529,306

[45] Date of Patent: Jul. 16, 1985

[54] APPARATUS AND METHOD FOR POLYMER MELT STREAM ANALYSIS

[75] Inventors: Lawrence B. Kilham, Secaucus; David W. Riley, Plainfield, both of N.J.

[73] Assignee: Flow Vision, Inc., Clifton, N.J.

[21] Appl. No.: 503,493

[22] Filed: Jun. 13, 1983

[51] Int. Cl.³ ............................................. G01N 21/89
[52] U.S. Cl. .................................. 356/237; 250/574; 356/338
[58] Field of Search ............... 356/237, 238, 239, 340, 356/338, 440, 441; 250/573, 574, 575, 227; 377/10, 11; 358/106, 107; 350/96.24, 96.25, 96.26

[56] References Cited

U.S. PATENT DOCUMENTS

| | | | |
|---|---|---|---|
| 3,758,787 | 9/1973 | Sigrist | 356/340 |
| 3,864,044 | 2/1975 | Lyshkow | 250/573 X |
| 4,043,669 | 8/1977 | Gehatia et al. | 356/340 |
| 4,075,462 | 2/1978 | Rowe | 377/10 |
| 4,139,306 | 2/1979 | Norton | 356/430 |
| 4,395,676 | 7/1983 | Hollinger et al. | 377/10 X |
| 4,500,793 | 2/1985 | Kuramoto | 356/414 X |

Primary Examiner—Vincent P. McGraw
Assistant Examiner—Robert D. V. Thompson, III
Attorney, Agent, or Firm—Samuelson & Jacob

[57] ABSTRACT

Apparatus and method for the analysis of a stream of molten polymer for the presence of unwanted voids, gels and particles of solids by observation of the stream, utilizing an observation probe and an illuminating probe placed at an illuminating angle to the observation probe so as to establish an image observable at an observation point remote from the stream.

36 Claims, 7 Drawing Figures

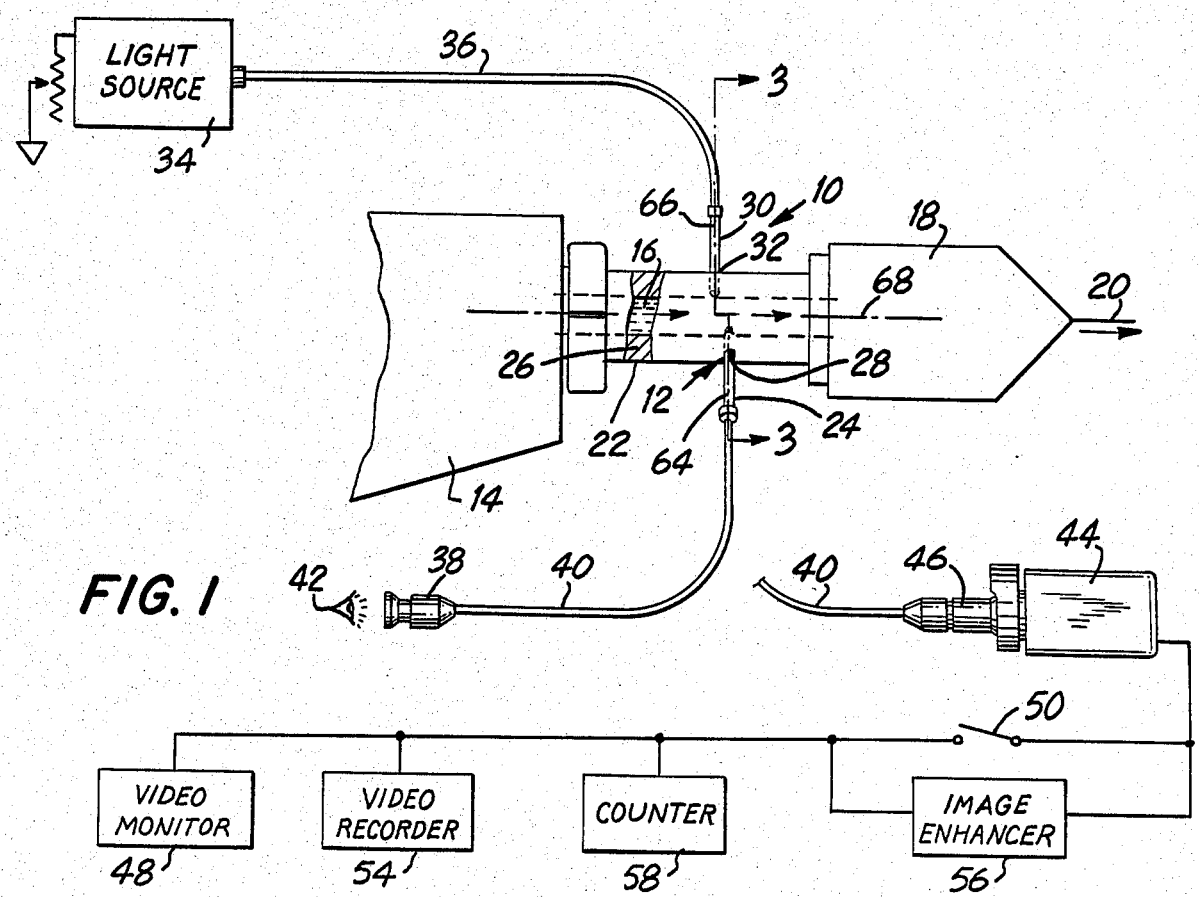
FIG. 1
FIG. 2
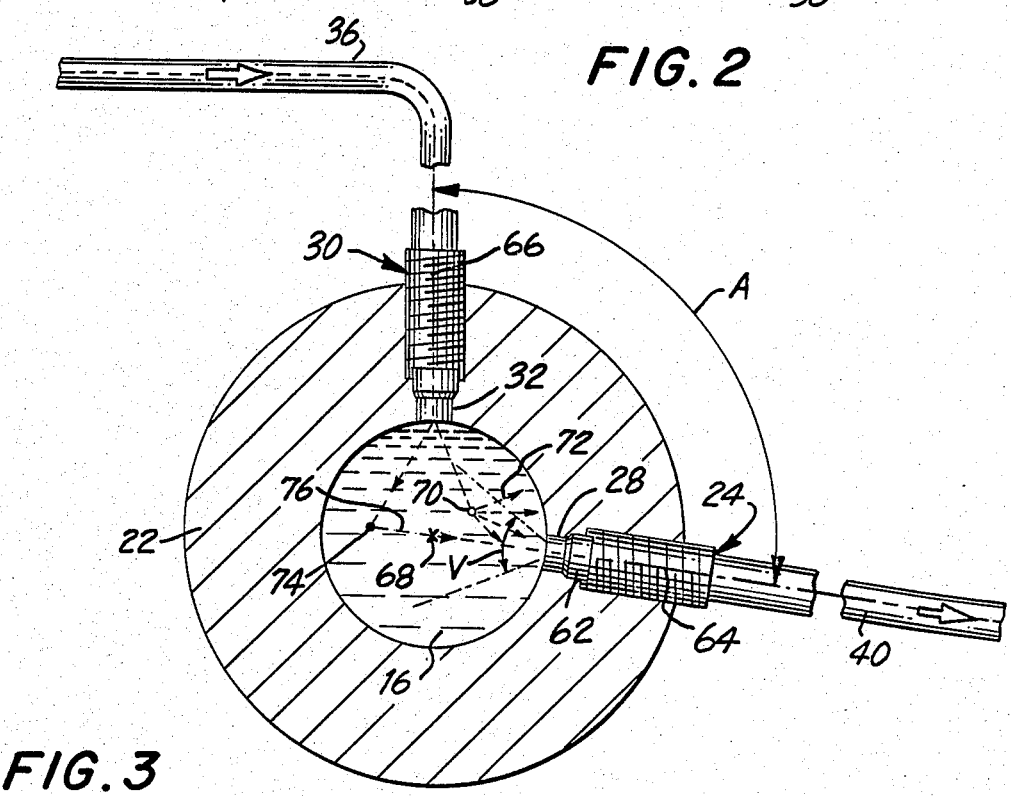
FIG. 3

APPARATUS AND METHOD FOR POLYMER MELT STREAM ANALYSIS

The present invention relates generally to the control of quality in the extrudate of plastics extruders and pertains, more specifically, to the analysis of the stream of molten polymer emanating from a plastics extruder for the presence of unwanted discontinuities or particulate matter in the melt stream.

The presence of gels, voids, carbon particles and other forms of discontinuities or particulate matter in molten polymers will affect the quality of finished end products manufactured from the molten polymers. In particular, thin films made from molten polymers cannot tolerate the presence of such discontinuities and particulate matter in large numbers or in large sizes relative to the dimensions of the film itself without severely degrading the quality of the film. It is therefore advantageous to analyze the molten polymer as it passes from the melting apparatus, such as a plastics extruder, to a forming apparatus, such as a mold or die, to enable determination of the number and size of any discontinuities or particulate matter in the melt stream so that appropriate corrections can be made before excessive quantities of the end product are produced.

While the advantages in determining the presence of discontinuities or particulate matter in a melt stream and characterizing the unwanted elements in terms of number, size and kind have been recognized, difficulties have been encountered in accomplishing such an analysis in a practical and economical manner, primarily because of the nature of the problem. Typically, molten polymer flows along a melt flow channel under high pressure (usually within the range of about 1,000 to 10,000 psi) and high temperature (about 250° to 800° F.). The polymers themselves often are highly corrosive and many have rather poor optical transmission properties. As a result, an effective, practical system heretofore has not been made available for widespread use, despite the fact that various approaches have been tried or suggested. Among these various approaches are: ultrasonic echo and ultrasonic beam breaking; infrared detection of temperature differentials; optical observation using light directed into the melt stream via a single channel used for observations as well as for a source of illumination; and laser scanning.

Ultrasonic echo or beam breaking techniques are limited in effectiveness due to the relatively long wave length of ultrasound in the polymer medium, which restricts resolution to voids or particles greater than about seven to twelve mils in diameter. It is desirable to enable the analysis to resolve particles and voids down to one mil or less in diameter.

Infrared detection techniques serve to analyze only the portion of the melt stream nearest the surface at the point of observation. It would be advantageous to analyze the meltstream to a depth of at least six inches. In addition, infrared detection techniques do not provide good contrast or acceptable resolution for small particles or voids, the smallest particles or voids readily detected by infrared being approximately twenty to fifty mils in diameter.

Optical observations with lighting provided via the viewing port, or even with back lighting, have very poor contrast and very little depth of field and therefore have provided very little information of value in analyzing the melt stream.

Laser scanning has been used for analyzing finished plastic film and sheet to detect the presence of gels, voids, and other imperfections. The use of such techniques in the analysis of a melt stream would require expensive scanning mechanisms, such as rotating mirror sets, which mechanisms would not be practical in the high temperature environment adjacent the melt stream. Furthermore, the laser is a monochromatic device and would not provide valuable color information pertaining to particles present in the melt stream.

The present invention takes advantage of the characteristic of nearly all of the commonly available commercial polymers which renders these polymers essentially transparent when heated to melting, even though the polymer when in its solid or crystalline state may be practically opaque.

It is an object of the present invention to provide apparatus and method for the analysis of a stream of molten polymer which enable an accurate and detailed determination of the presence and identification of unwanted discontinuities or particulate matter in the melt stream.

Another object of the invention is to provide a practical apparatus and method for the analysis of a stream of molten polymer which will operate effectively and reliably in the environment of the high pressure, high temperature melt stream to detect and identify unwanted discontinuities and particulate matter in the melt stream.

Still another object of the invention is to provide apparatus and method of the type described and which are adapted easily to manufacturing equipment presently in use, for enabling improved results with minimal modifications.

Yet another object of the invention is to provide simplified apparatus and method of the type described and which utilize a good deal of known, reliable technology in an environment heretofore not explored with such technology for attaining accurate and detailed information pertaining to the presence of unwanted elements in a stream of molten polymer.

A further object of the invention is to provide apparatus and method of the type described and which permit access to the melt stream for analysis in a wide variety of manufacturing machinery, even where access sites are limited and difficult to reach.

A still further object of the invention is to provide apparatus and method of the type described and which utilize relatively inexpensive equipment and techniques so as to enable widespread practical applications.

Yet a further object of the invention is to provide apparatus and method of the type described and which enable ease of operation so that even operators of limited skill are able to obtain improved results with minimal effort and expense.

The above objects, as well as still further objects and advantages, are attained by the present invention which may be described briefly as apparatus and method for the analysis of a stream of molten polymer in a longitudinal path of travel within an axially-extending walled conduit for the presence of unwanted elements in the molten polymer stream in the form of transparent and translucent elements, such as voids and some gels, and opaque elements, such as particles of solids and other gels, by observation of the lateral cross-section of the molten polymer stream. The apparatus comprises an observation probe extending into the wall of the conduit and including an observation window juxtaposed with the path of travel of the stream of molten polymer at a first location adjacent the lateral cross-section, and at least one illuminating probe extending into the wall of the conduit and including an illumination window juxtaposed with the path of travel of the stream of molten polymer at a second location adjacent the lateral cross-section and spaced from the first location at an illuminating angle about the longitudinal axis of the conduit, the observation probe including a focal plane adjacent the observation window and spaced therefrom, an objective lens between the observation window and the focal plane for focusing an image of at least a portion of the lateral cross-section of the stream of molten polymer upon the focal plane, and image-conducting means for conducting the image to an observation point remote from the observation window. The method includes the steps of illuminating the stream of molten polymer at a given location adjacent the lateral cross-section, establishing an image of the illuminated stream of molten polymer as viewed at a further location spaced from the given location at an illuminating angle about the longitudinal axis of the conduit, and conducting the image to an observation point remote from the stream.

The invention will be understood more fully, while still further objects and advantages will become apparent, in the following detailed description of preferred embodiments of the invention illustrated in the accompanying drawing, in which:

FIG. 1 is a semi-diagrammatic illustration of a typical system utilizing an apparatus constructed and operated in accordance with the present invention;

FIG. 2 is a semi-diagrammatic illustration of an alternate arrangement for a portion of the apparatus;

FIG. 3 is an enlarged cross-sectional view taken along line 3—3 of FIG. 1;

Figure 4:
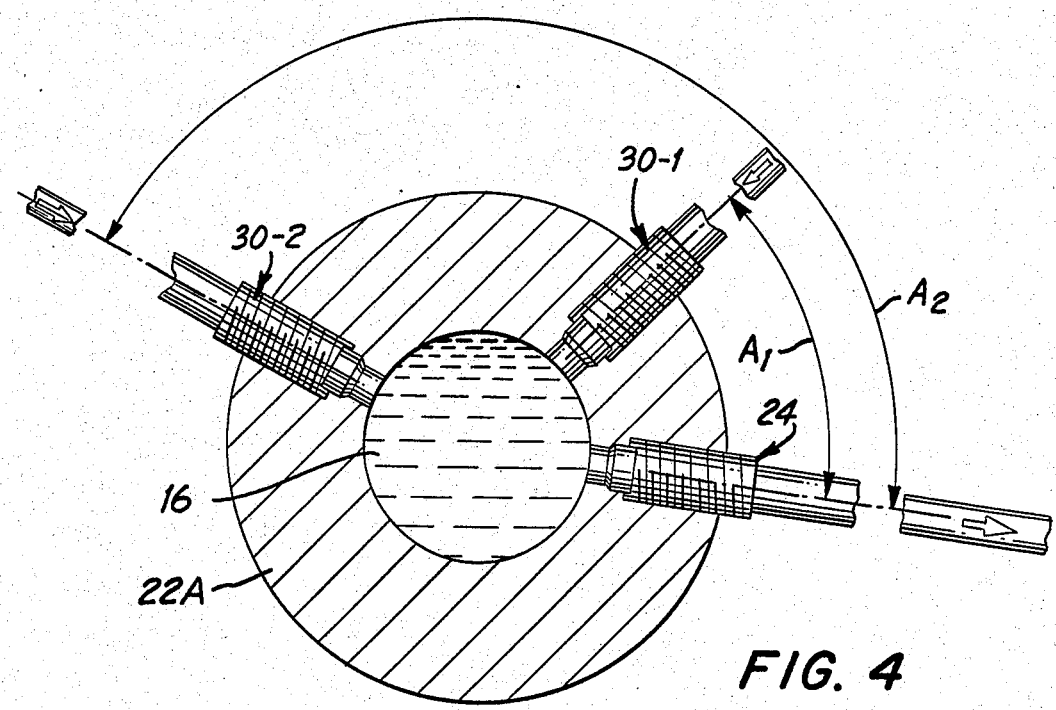
FIG. 4 is an enlarged cross-sectional view similar to FIG. 3 and showing an alternate arrangement.

Referring now to the drawing, and especially to FIG. 1 thereof, a system 10 is illustrated diagrammatically and includes an apparatus 12 constructed and operated in accordance with the present invention. System 10 includes an extruder 14 which feeds a molten polymer 16 to an extrusion die 18 to produce an end product in the form of a film 20 shown exiting from the die 18. A casing 22 provides an axially-extending walled conduit for conducting the molten polymer 16 in a stream along a longitudinal path of travel between the extruder 14 and the die 18.

Apparatus 12 includes an observation probe 24 which extends through the wall 26 of casing 22 at an observation location 28 adjacent the stream of molten polymer 16 to enable visual observation of the melt stream in the casing 22. An illuminating probe 30 extends through the wall 26 of casing 22 at an illuminating location 32, also adjacent the stream of molten polymer 16, to illuminate the melt stream for visual observation through the observation probe 24. The illuminating probe 30 is coupled to a light source 34 by means of a light-conducting guide 36, preferably in the form including a fiber optic bundle, which transmits light from light source 34 to illuminating probe 30. The observation probe 24 is coupled to an observation means, illustrated in the form of an eyepiece 38, by image-conducting means shown in the form of a coherent fiber optic bundle in a cable 40 so that images will be conducted from the observation probe 24 to the remote eyepiece 38 for visual observation, as illustrated by an eye 42, in a manner which will be described in greater detail below.

In a typical system 10, casing 22 is constructed of steel and has an inside diameter of about one to six inches, and wall 26 has a thickness of about one-half to two inches. Light source 34 preferably includes a source of high intensity visible light, such as a halogen lamp of about 150 watts, providing white light (typically 3250° K.), focused by an optical system into the fiber optic bundle of light-conducting guide 36. The fiber optic bundle is a non-coherent bundle having a diameter of about one-eighth to one-quarter inch. Eyepiece 38 provides 7× to 10× of magnification for direct viewing of the image established in the observation probe 24.

Alternately, as seen in FIG. 2, the optical image established in the observation probe 24 may be conducted by cable 40 to a video camera 44 coupled to cable 40 by a lens system 46, typically having a 2× magnification. Video camera 44 will convert the received optical image into electronic information which may be forwarded directly to a video monitor 48, via switch 50. The video monitor 48 then will display an image at a further remote observation location for viewing by an observer to determine the quality of the extrudate emanating from extruder 14. A video recorder 54 may be employed to record the images. Optionally, an image enhancing means 56 may be utilized to enhance the image for increased accuracy and to aid in the analysis of the observed image. As a further option, an event counter 58 may be placed in the circuit to record information pertaining to the image, as will be described below.

Turning now to FIG. 3, the enlarged cross-section taken through casing 22 illustrates the relative arrangement of the probes 24 and 30 and the manner in which the stream of molten polymer 16 is observed for analysis. Observation probe 24 is located at 28 and has an optical system within the tip 62 thereof which enables a view of the stream of molten polymer 16 within a viewing angle V. The optical system enables angle V to be about 40° to 70°. Where casing 22 provides the melt stream with a generally round cross-section, as seen in FIG. 3, viewing angle V enables observation probe 24 to view approximately 30% to 60% of the total cross-section of the melt stream. In some instances, casing 22 will have an elliptical cross-section which provides the same cross-sectional area, but by alignment of the longitudinal axis 64 of the observation probe 24 generally with the major axis of the elliptical cross-section, the viewing angle V will enable the observation probe to view a greater portion of the total cross-section of the melt stream, up to about 80% to 90%, than with a round cross-section. It is noted, however, that larger viewing angles generally are not required because gels, voids, particles and other elements to be observed tend to flow along the center of the meltstream, due to the nature of the forces in the non-Newtonian flow present in the molten polymer, and it is not essential, for most analyses, to view the outer periphery of the melt stream.

Illuminating probe 30 is located relative to the observation probe 24 at an illuminating angle A between the longitudinal axis 64 of the observation probe 24 and the longitudinal axis 66 of the illuminating probe 30 about the longitudinal axis 68 of the conduit provided by casing 22. It has been found that the particular choice of illuminating angle A facilitates the viewing of specific types of unwanted elements in the melt stream. Thus, by placing the probes 24 and 30 so that angle A is in the range of about 90° to 180°, the observation of transparent and translucent elements, such as voids and some gels, is enhanced, while at an angle A of about 90° or less the observation of opaque elements, such as carbon particles, other gels and other contaminants, is enhanced. The range of angle A between about 90° to 180° appears to employ a light scattering phenomenon which better serves to identify transparent and translucent elements for analysis, while the range of angle A up to 90° appears to employ a light reflection phenomenon which better serves to identify opaque elements in the melt stream. In the embodiment shown in FIG. 3, the illuminating angle A is about 90° and both the light scattering phenomenon and the light reflecting phenomenon are illustrated. Thus, light impinging upon an element in the form of a transparent void 70 is scattered and the scattered light 72 is observed to detect the transparent void 70 and to identify the element as a transparent void. Light impinging upon an element in the form of an opaque particle 74 is reflected and the reflected light 76 is observed to detect and identify the element as an opaque particle.

Where the melt stream is to be analyzed for both transparent or translucent elements and for opaque elements, two illuminating probes may be employed, with each illuminating probe being placed at an optimum illuminating angle for the particular elements to be observed. As seen in FIG. 4, an alternate casing 22A has an observation probe 24 and two illuminating probes 30-1 and 30-2. Illuminating probe 30-1 is placed at an illuminating angle $A_1$ which is the optimum angle for the observation of opaque elements, while illuminating probe 30-2 is placed at an illuminating angle $A_2$ which is the optimum angle for the observation of transparent and translucent elements. Empirical observations have determined that the optimum angle $A_1$ is in the range of about 10° to 45°, considering the practical limitations imposed by the dimensions of the actual component parts. Similarly, it has been determined that the optimum angle $A_2$ is in the range about 135° to 180°. Each illuminating probe 30-1 and 30-2 is coupled to a corresponding independent light source (not shown), each light source being similar to light source 34. An operator-observer then can operate the light sources alternately, while observing the melt stream, to analyze the observed elements and determine the nature of the elements; that is, the elements can be identified as voids, gels or particles by an analysis of the images of the elements produced by the different illuminating angles. Multiple illuminating probes also may be employed to increase the light available in the melt stream and enhance the observed images.

It is noted that the placement of illuminating probes at various illuminating angles may tend to direct light from a particular illuminating probe directly into the observation probe, thereby degrading the observed images. In order to reduce such a tendency, the plane of the longitudinal axis 64 of the observation probe 24 is spaced axially from the plane of the axis 66 of the illuminating probe 30. As seen in FIG. 1, observation probe 24 is spaced downstream of illuminating probe 30.

Figure 5:
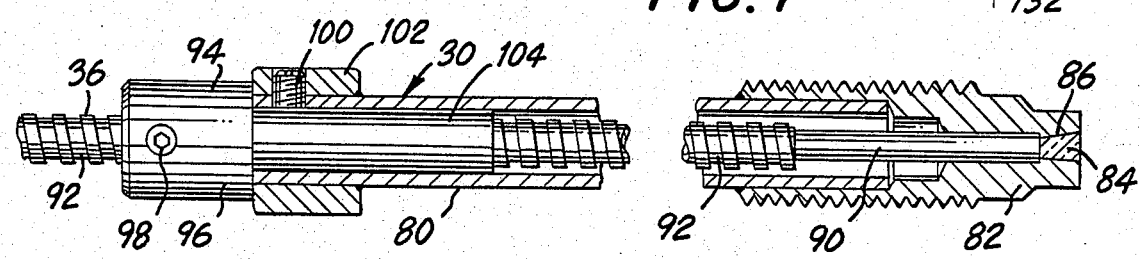
FIG. 5 is a longitudinal cross-sectional view of an illuminating probe of the apparatus.

Referring now to FIG. 5, illuminating probe 30 must withstand elevated temperatures and pressures and is constructed accordingly. An outer housing 80, preferably of stainless steel, is affixed to a threaded tip 82, as by welding. The threaded tip 82 extends through the casing 22 and presents an illuminating window 84 juxtaposed with the path of travel of the stream of molten polymer 16. Illuminating window 84 preferably is constructed of sapphire to withstand temperatures of about 800° F. and pressures of about 10,000 psi, as well as the abrasion of the flowing molten polymer. A tapered surface 86 assures that the window 84 remains seated and sealed within the tip 82, even under elevated pressures. The fiber optic bundle is shown at 90 and extends to the window 84. A protective sheath 92 surrounds the fiber optic bundle 90 and forms the outer covering of light-conducting guide 96. A retainer 94 is secured to the sheath 90 at collar portion 96 thereof by means of a set screw 98, and a second set screw 100 extends through a second collar 102 welded to the housing 80 to secure the housing to a tubular portion 104 of retainer 94.

Figure 6:
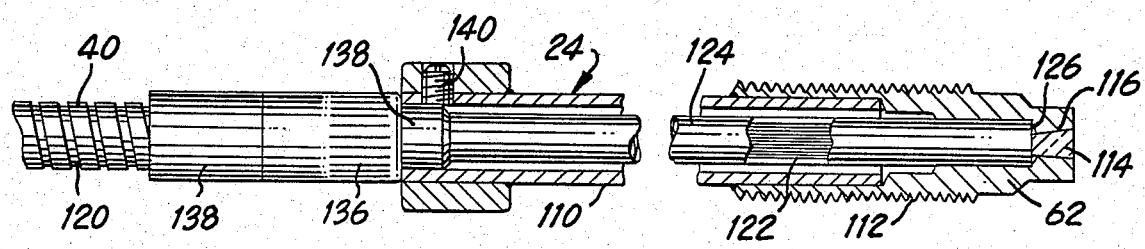
FIG. 6 is a longitudinal cross-sectional view of an observation probe of the apparatus.
Figure 7:
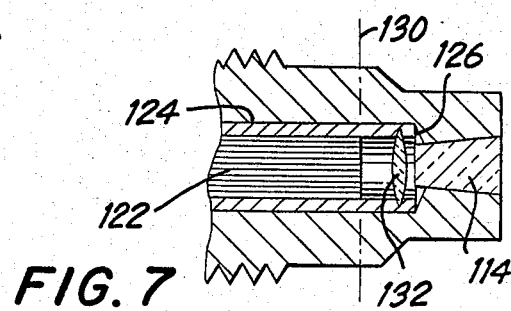
FIG. 7 is an enlarged fragmentary view of a portion of FIG. 6.

Turning now to FIGS. 6 and 7, the observation probe 24 also includes an outer housing 110, preferably of stainless steel, affixed to tip 62, as by welding. Tip 62 is threaded at 112 and extends through the casing 22 to present an observation window 114 juxtaposed with the path of travel of the stream of molten polymer 16. Observation window 114 also is constructed of sapphire to withstand the temperatures and pressures, as well as the abrasion, to which the window 114 will be subjected, and includes a tapered surface 116 to assure that the window remains seated and sealed within tip 62. A protective sheath 120 surrounds the coherent fiber optic bundle, shown at 122, and serves as the outer covering of cable 40. A sleeve 124 surrounds the coherent fiber optic bundle 122 and extends to a far end 126 adjacent window 114, and the coherent fiber optic bundle terminates at a plane 130. The optical system within tip 62 includes an objective lens 132 carried by the sleeve 124 at far end 126 for focusing images passing through window 114 from the stream of molten polymer upon plane 130 so that the focused images will be conducted by the coherent fiber optic bundle 122 to the remote observation means. Thus, plane 130 is a focal plane for images to be viewed and coincides with the terminal end of the coherent fiber optic bundle 122.

In order to enable objective lens 132 to focus images at various distances from window 114 into the melt stream, sleeve 124 is selectively movable in axial directions to move objective lens 132 axially relative to plane 130. Thus, a knurled collar 136 is mounted for rotation upon a retainer 138 affixed to housing 110 by set screw 140 and is threadedly coupled to sleeve 124 such that selective rotation of knurled collar 136 will move sleeve 124 axially to advance or retract objective lens 132 relative to plane 130. In this manner, various portions of the cross-section of the melt stream may be observed for analysis. Alternately, objective lens 132 may be provided with a depth of field great enough to focus, at the plane 130, an observable image located at essentially any location across the full lateral cross-section of the stream of molten polymer 16.

As noted above, the characteristic of nearly all commonly available commercial polymers which renders these polymers essentially transparent when heated to melting enables the present invention to find use with nearly all commercial polymers. Of course, highly pigmented or filled polymers usually will not fall within the above category.

Thus, apparatus 12 provides a relatively simple and inexpensive arrangement and method for analyzing the stream of molten polymer 16 to determine the nature and number of unwanted elements in the form of discontinuities or particles in the melt stream. The unwanted elements actually are observed and inspected visually and changes can be made in the operation of the extruder 14 to correct conditions so as to reduce the presence of unwanted elements. The images conducted from the observation probe 24 may be viewed directly or may be viewed upon a video monitor, after enhancement to further increase the accuracy with which the unwanted elements are counted and identified. A count of the number and types of unwanted elements may be made electronically as a means for automatic monitoring of a particular manufacturing operation. Thus, the simplicity and versatility of apparatus 12 enables the apparatus to fill a widespread need in a practical manner.

It is to be understood that the above description of embodiments of the invention is provided by way of example only. Various details of design and construction may be modified without departing from the true spirit and scope of the invention as set forth in the appended claims.

The embodiments of the invention in which an exclusive property or privilege is claimed are as follows:

1. Apparatus for the analysis of a stream of molten polymer in a longitudinal path of travel within an axially-extending walled conduit for the presence of unwanted elements in the molten polymer stream in the form of transparent and translucent elements, such as voids and some gels, and opaque elements, such as particles of solids and other gels, by observation of the lateral cross-section of the molten polymer stream, the apparatus comprising:

an observation probe extending into the wall of the conduit and including an observation window juxtaposed with the path of travel of the stream of molten polymer at a first location adjacent the lateral cross-section; and at least one illuminating probe extending into the wall of the conduit and including an illumination window juxtaposed with the path of travel of the stream of molten polymer at a second location adjacent the lateral cross-section and spaced from the first location at an illuminating angle about the longitudinal axis of the conduit;

the observation probe including a focal plane adjacent the observation window and spaced therefrom, an objective lens between the observation window and the focal plane for focusing an image of at least a portion of the lateral cross-section of the stream of molten polymer upon the focal plane, and image-conducting means for conducting the image to an observation point remote from the observation window.

2. The invention of claim 1 wherein the illuminating angle is about 90° to 180°.

3. The invention of claim 1 wherein the illuminating angle is up to about 90°.

4. The invention of claim 3 wherein the illuminating angle is about 10° to 45°.

5. The invention of claim 1, 2, 3 or 4 wherein the observation window is spaced axially from the illumination window.

6. The invention of claim 5 wherein the observation window is located axially downstream of the illumination window.

7. The invention of claim 1, 2, 3 or 4 including observation means at the observation point.

8. The invention of claim 1, 2, 3 or 4 wherein the image-conducting means includes light-conducting means for conducting the image optically to the observation point.

9. The invention of claim 8 wherein the image-conducting means includes a coherent fiber optic bundle extending between the focal plane and the observation point.

10. The invention of claim 9 including observation means at the observation point.

11. The invention of claim 10 wherein the observation means includes a video camera for converting the optical image into electronic information pertaining to the optical image.

12. The invention of claim 11 wherein the observation window is spaced axially from the illumination window.

13. The invention of claim 12 wherein the observation window is located axially downstream of the illumination window.

14. The invention of claim 1, 2, 3 or 4 including means for adjusting the spacing between the objective lens and the focal plane so as to enable selection of the portion of the lateral cross-section across the stream to be focused upon the focal plane.

15. The invention of claim 1, 2, 3 or 4 wherein the depth of field of the objective lens is such that an observable image extending essentially across the full lateral cross-section of the stream of molten polymer is focused upon the focal plane.

16. The invention of claim 15 wherein the image-conducting means includes a coherent fiber optic bundle extending between the focal plane and the observation point.

17. The invention of claim 16 wherein including observation means at the observation point.

18. The invention of claim 17 wherein the observation means includes a video camera for converting the optical image into electronic information pertaining to the optical image.

19. The invention of claim 18 wherein the observation window is spaced axially from the illumination window.

20. The invention of claim 19 wherein the observation window is located axially downstream of the illumination window.

21. The invention of claim 1, 2, 3 or 4 wherein the objective lens includes a viewing angle of about 40° to 70°.

22. The invention of claim 21 wherein the depth of field of the objective lens is such that an observable image extending essentially across the full lateral cross-section of the stream of molten polymer is focused upon the focal plane.

23. The invention of claim 22 wherein the image-conducting means includes a coherent fiber optic bundle extending between the focal plane and the observation point.

24. The invention of claim 23 including observation means at the observation point.

25. The invention of claim 24 wherein the observation means includes a video camera for converting the optical image into electrical information pertaining to the optical image.

26. The invention claim 25 wherein the observation window is spaced axially from the illumination window.

27. The invention of claim 26 wherein the observation window is located axially downstream of the illumination window.

28. The method for analyzing a stream of molten polymer in a longitudinal path of travel within an axially-extending conduit for the presence of unwanted elements in the molten polymer stream in the form of transparent and translucent elements, such as voids and some gels, and opaque elements, such as particles of solids and other gels, by observation of the lateral cross-section of the molten polymer stream, the method comprising the steps of:

juxtaposing observation means with the stream of molten polymer at a first location adjacent the lateral cross-section of the molten polymer stream;

juxtaposing illuminating means with the stream of molten polymer at at least one further location adjacent the lateral cross-section of the molten polymer stream and spaced from the first location at an illuminating angle about the longitudinal axis of the conduit to illuminate at least a portion of the lateral cross-section of the molten polymer stream;

establishing an image, adjacent the stream of molten polymer, of at least a portion of the lateral cross-section of the molten polymer stream as illuminated by the illuminating means and viewed by the observation means; and conducting the image from adjacent the stream of molten polymer to an observation point remote from the molten polymer stream.

29. The invention of claim 28 wherein the illuminating angle is about 90° to 180°.

30. The invention of claim 28 wherein the illuminating angle is up to about 90°.

31. The invention of claim 30 wherein the illuminating angle is about 10° to 45°.

32. The invention of claim 29, 30 or 31 wherein the further location is spaced axially from the first location.

33. The invention of claim 32 wherein the further location is located axially downstream of the first location.

34. The invention of claim 29, 30 or 31 wherein the image is conducted optically to the observation point remote from the stream and further including the step of converting the image at the remote observation point into electronic information pertaining to the image.

35. The invention of claim 34 wherein the further location is spaced axially from the first location.

36. The invention of claim 35 wherein the first location is located axially downstream of the further location.

* * * * *